(12) United States Patent
DeShazo

(10) Patent No.: US 11,493,556 B2
(45) Date of Patent: Nov. 8, 2022

(54) METHODS OF DETERMINING BATTERY LIFE IN AN IMPLANTABLE MEDICAL DEVICE

(71) Applicant: ADVANCED NEUROMODULATION SYSTEMS, INC., Plano, TX (US)

(72) Inventor: Daran DeShazo, Lewisville, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 70 days.

(21) Appl. No.: 16/364,918

(22) Filed: Mar. 26, 2019

(65) Prior Publication Data

US 2020/0309859 A1 Oct. 1, 2020

(51) Int. Cl.
| | |
|---|---|
| G08B 21/00 | (2006.01) |
| G01R 31/36 | (2020.01) |
| G01R 31/378 | (2019.01) |
| G01R 31/371 | (2019.01) |
| A61B 5/07 | (2006.01) |
| A61N 1/378 | (2006.01) |
| A61N 1/372 | (2006.01) |
| A61N 1/02 | (2006.01) |
| A61N 1/36 | (2006.01) |

(52) U.S. Cl.
CPC .......... *G01R 31/3647* (2019.01); *A61B 5/076* (2013.01); *A61N 1/025* (2013.01); *A61N 1/378* (2013.01); *A61N 1/37235* (2013.01); *G01R 31/371* (2019.01); *G01R 31/38* (2019.01); *A61B 2560/0204* (2013.01); *A61N 1/3605* (2013.01)

(58) Field of Classification Search
CPC .. G01R 31/3647; G01R 31/38; G01R 31/371; A61B 5/076; A61B 2560/0204; A61N 1/025; A61N 1/37235; A61N 1/378; A61N 1/3605
USPC ...................................................... 340/636.1
See application file for complete search history.

(56) References Cited

U.S. PATENT DOCUMENTS

| 5,477,050 | A | * | 12/1995 | Kronenberg | ............ G01T 1/026 250/336.1 |
|---|---|---|---|---|---|
| 5,925,068 | A | * | 7/1999 | Kroll | .................... A61N 1/3975 607/29 |
| 6,609,031 | B1 | | 8/2003 | Law et al. | |
| 7,180,760 | B2 | | 2/2007 | Varrichio et al. | |
| 7,212,110 | B1 | | 5/2007 | Martin et al. | |
| 7,215,999 | B1 | * | 5/2007 | Shahandeh | ........ G01R 31/3648 607/27 |

(Continued)

*Primary Examiner* — Naomi J Small
(74) *Attorney, Agent, or Firm* — Norton Rose Fulbright US LLP

(57) ABSTRACT

An implantable medical device (IMD), includes a processor for controlling the IMD; circuitry for providing therapeutic or diagnostic medical operations for a patient; wireless communication circuitry for conducting wireless communications; a non-rechargeable battery; and device power control circuitry. The device power control circuitry includes at least one capacitor; charging control circuitry for switching between charging the at least one capacitor using the non-rechargeable battery and discharging the at least one capacitor to provide power for device operations. The IMD is configured to maintain a count related to a number of times of discharge of the at least one capacitor to provide an end-of-life estimation for the non-rechargeable battery.

20 Claims, 10 Drawing Sheets

(56) References Cited

U.S. PATENT DOCUMENTS

| | | |
|---|---|---|
| 7,937,158 B2 | 5/2011 | Erickson et al. |
| 8,179,190 B2 | 5/2012 | Tranchina et al. |
| 9,635,478 B1 * | 4/2017 | Mazanec ............... H04R 25/305 |
| 9,894,691 B1 | 2/2018 | Hellman et al. |
| 2010/0058480 A1 * | 3/2010 | Hedberg ................ G16H 40/63 |
| | | 705/50 |
| 2010/0188049 A1 * | 7/2010 | Haddani ............ G01R 31/3832 |
| | | 320/128 |
| 2011/0307033 A1 * | 12/2011 | Michaels ............. A61N 1/3708 |
| | | 607/60 |
| 2013/0110428 A1 * | 5/2013 | Sun .................... G01R 31/3842 |
| | | 702/63 |
| 2014/0278168 A1 * | 9/2014 | Rogers ............... G01R 31/3835 |
| | | 702/63 |
| 2015/0217122 A1 * | 8/2015 | Leskosek ............... A61N 1/365 |
| | | 607/7 |
| 2017/0003356 A1 * | 1/2017 | Kaib .................. A61N 1/3708 |
| 2017/0143977 A1 * | 5/2017 | Kaib ...................... A61N 1/046 |
| 2017/0157395 A1 * | 6/2017 | Thompson-Nauman .................... |
| | | A61N 1/36521 |
| 2020/0246626 A1 * | 8/2020 | Labbe ................. A61N 1/3615 |

* cited by examiner

METHODS OF DETERMINING BATTERY LIFE IN AN IMPLANTABLE MEDICAL DEVICE

BACKGROUND

Implantable medical devices have improved how medical care is provided to patients with certain types of chronic illnesses and disorders. For example, implantable cardiac devices improve cardiac function in patients with heart disease thereby raising quality of life and reducing morality rates, Implantable neurostimulators can provide pain reduction for chronic pain patients and reduce motor difficulties in patients with Parkinson's disease and other movement disorders. A variety of other medical devices are proposed and are in development to treat other disorders in a wide range of patients.

Neural activity in the brain can be influenced by electrical energy that is supplied from a stimulation system pulse generator or other waveform generator. Various patient perceptions and/or neural functions can be promoted or disrupted by applying an electrical or magnetic signal to the brain. Medical researchers and clinicians have attempted to treat various neurological conditions using electrical or magnetic stimulation signals to control or affect brain functions. For example, Deep Brain Stimulation (DBS) may reduce some of the symptoms associated with Parkinson's Disease, which results in movement or muscle control problems and is debilitating to a great number of individuals worldwide.

A stimulation system pulse generator may be provided in various configurations, such as an implanted pulse generator (IPG). A typical IPG configuration comprises a surgically implanted, internally-powered pulse generator and multielectrode lead. The implanted pulse generator may commonly be encased in a hermetically sealed housing and surgically implanted in a subclavicular location. An electrode assembly may be implanted to deliver stimulation signals to a stimulation site. The electrode assembly is coupled to the pulse generator via biocompatibly sealed lead wires. A power source, such as a battery, is contained within the housing of the pulse generator.

Since a battery has a finite charge storage capacity, a battery will expire or become depleted, thereby interrupting the patient's treatment. Various types of neural stimulation systems may include a nonchargeable battery that may last approximately two to three years. After an implanted battery is exhausted, another surgery is typically required to replace the pulse generator and/or battery. Accordingly, it is critical for medical personnel and clinicians to know when the battery in an implanted pulse generator has a low charge level and requires replacement. It is difficult to measure the battery charge directly on an implanted device. Existing systems provide a voltage or longevity estimate on a programmer for the implantable device, such as a bar shown on a panel display, that considers the initial battery voltage as well as programmed parameters, telemetry usage, and other factors affecting current drain. These displays use battery voltage as an indicator of the battery condition. However, battery voltage rundown is non-linear and fluctuates based on changes in the programmed settings, percent pacing, and high voltage charging. Assuming a constant current drain, there are periods in the implanted battery's life in which the voltage drops relatively quickly and other periods where the voltage remains relatively constant. Depending on the circuitry and battery chemistry, using battery voltage alone to represent the remaining capacity may give an unreliable picture of the remaining longevity.

The implantable device may measure voltage across a low value sense resister and integrate that voltage to determine the charge taken from the battery. This estimated value can be transmitted to the programmer to be shown to medical personnel or clinicians as a fuel gauge. However, because the signal that is being measured is extremely small, the fuel gauge has to eliminate any offset in the measurement system. The offset may prevent the fuel gauge from measuring voltage at all or may require complicated offset correction algorithms in the software, which require more power. To eliminate the offset, the fuel gauge may need to add trims, which are a manufacturing burden, or may perform a sampling/offset correction scheme. Because the implanted devices may be extremely bursty (i.e., have a long period with a very low background current and then large spikes or peaks of high current) due to communication or other operations. The fuel gauge must sample at a fast rate to catch these very short events and/or must have specific external filtering to try to average out the bursts. Existing fuel gauges are not optimal since they require offset corrections and use too much power.

SUMMARY

Figure 1:
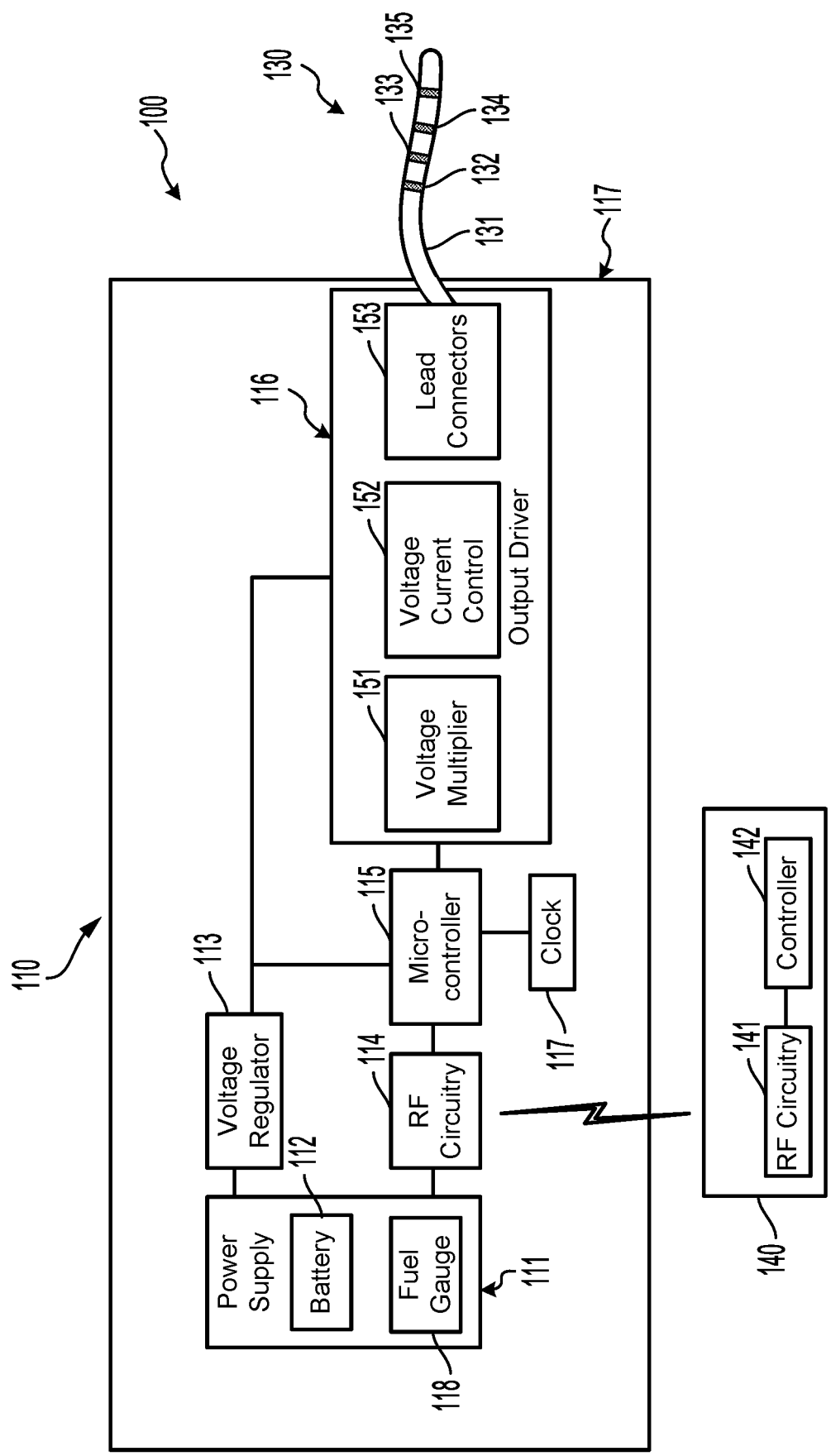
FIG. 1 depicts a neurostimulation system that is adapted according to an example embodiment and is shown as a high-level functional block diagram.

In one embodiment, an implantable medical device (IMD), comprises: a processor for controlling the IMD; circuitry for providing therapeutic or diagnostic medical operations for a patient: wireless communication circuitry for conducting wireless communications; a non-rechargeable battery; and device power control circuitry comprising: at least one capacitor; charging control circuitry for switching between charging the at least one capacitor using the non-rechargeable battery and discharging the at least one capacitor to provide power for device operations; wherein the IMD is configured to maintain a count related to a number of times of discharge of the at least one capacitor to provide an end-of-life estimation for the IMD.

In some embodiments, the device operations include therapy or diagnostic operations and wireless communication operations.

The device power control circuitry may further comprise: a comparator coupled to the at least one capacitor and to a reference voltage, the comparator configured to generate an output signal when a voltage across the capacitor is equal to or less than the reference voltage, wherein the capacitor is temporarily coupled to the non-rechargeable battery in response to the comparator output signal. In some embodiments, in response to the comparator output signal, the capacitor is coupled to the non-rechargeable battery for a predetermined interval and is decoupled from the non-rechargeable battery after the predetermined interval. In some embodiments, in response to the comparator output signal, the capacitor is coupled to the non-rechargeable battery until a capacitor voltage reaches a power supply voltage and is decoupled from the non-rechargeable battery after reaching the power supply voltage. In some embodiments, the IMD comprises a counter circuit coupled to the comparator, the counter circuit configured to record a number of times the output signal is detected.

In some embodiments, the IMD comprises: memory for storing data and executable instructions, wherein the executable instructions comprise code for causing the processor to (1) monitor a comparator output, (2) couple the capacitor to the non-rechargeable battery when the comparator output signal is detected, and (3) decouple the capacitor from the non-rechargeable battery after reaching the power supply voltage.

In some embodiments, the IMD further comprises: memory for storing data and executable instructions, wherein the executable instructions comprise code for causing the processor to (a) conduct a communication session between the IMD and an external programming device, and (b) transmitting data from the IMD to the external programming device to end-of-life estimation data for the IMD. In some embodiments, the end-of-life estimation data comprises a count of comparator output signal detections.

In some embodiments, a method of operating an implantable medical device (IMD) after implantation in a patient, comprises: operating power control circuitry to power operations of the IMD, wherein the operating power control circuitry comprises (1) switchably coupling a non-rechargeable battery of the IMD to at least one capacitor to charge the at least one capacitor and (2) discharging the at least one capacitor to power device operations of the IMD, wherein the device operations include therapeutic or diagnostic operations performed by circuitry of the IMD; tracking data related to a number of times that the at least one capacitor has been discharged; conducting a communication session with a device external to the patient using wireless communication circuitry of the IMD; and communicating end-of-life estimation data to the device external to the patient.

In some embodiments, the method further comprises: comparing a capacitor voltage to a reference voltage; coupling the capacitor to the non-rechargeable battery when the capacitor voltage is equal to or less than the reference voltage; decoupling the capacitor from the non-rechargeable battery when the capacitor voltage is equal to a power source voltage or after a predetermined interval: monitoring an output of a comparator circuit; and closing a switch to couple the capacitor to the power source when a comparator output signal is detected. The method may further comprise: monitoring an output of a comparator circuit; and counting a number of times the comparator output signal is detected.

In some embodiments, an implantable medical device (IMD), comprises: a processor for controlling the IMD; circuitry for providing therapeutic or diagnostic medical operations for a patient; wireless communication circuitry for conducting wireless communications; a non-rechargeable battery; and device power control circuitry comprising: a plurality of capacitors; charging control circuitry for switching between charging one or more capacitors of the plurality of capacitors using the non-rechargeable battery and discharging one or more capacitors of the plurality of capacitors to provide power for device operations; wherein the IMD is configured to maintain a count related to a number of times of discharge of the plurality of capacitors to provide an end-of-life estimation for the IMD.

In some embodiment, the IMD further comprises: a comparator having a first input alternately coupled to the first capacitor and the second capacitor and having a second input coupled to a reference voltage, the comparator configured to generate an output signal when a first input voltage is equal to or less than the reference voltage, wherein the output signal is configured to swap which capacitor is coupled to the non-rechargeable battery and which capacitor is discharged to power device operations.

In some embodiments, in response to the comparator output signal, the first capacitor or the second capacitor is coupled to the non-rechargeable battery for a predetermined interval and is decoupled from the power supply after the predetermined interval. In some embodiment, in response to the comparator output signal, the first capacitor or the second capacitor is coupled to the non-rechargeable battery until a capacitor voltage reaches a power supply voltage and is decoupled from the power supply after reaching the power supply voltage. In some embodiments, the IMD further comprises: a counter coupled to the comparator, the counter configured to record a number of times the output signal is detected.

In some embodiments, the IMD further comprises: memory for storing data and executable instructions, wherein the executable instructions comprise code for causing the processor to (a) conduct a communication session between the IMD and an external programming device, and (b) transmitting data from the IMD to the external programming device to end-of-life estimation data for the IMD.

DETAILED DESCRIPTION

FIG. 1 depicts a neurostimulation system 100 that is adapted according to an example embodiment and is shown as a high-level functional block diagram. Neurostimulation systems are devices that generate electrical pulses and deliver the pulses to nerve tissue of a patient to treat a variety of disorders. Spinal cord stimulation (SCS) is the most common type of neurostimulation within the broader field of neuromodulation. In SCS, electrical pulses are delivered to nerve tissue of the spinal cord for the purpose of chronic pain control. While a precise understanding of the interaction between the applied electrical energy and the nervous tissue is not fully appreciated, it is known that application of an electrical field to spinal nervous tissue can effectively inhibit certain types of pain transmitted from regions of the body associated with the stimulated nerve tissue to the brain. Under certain stimulation conditions, applying electrical energy to the spinal cord associated with regions of the body afflicted with chronic pain can induce "paresthesia" (a subjective sensation of numbness or tingling) in the afflicted bodily regions. Certain stimulation patterns (such as Burst-DR™ stimulation provided by pulse generators of Abbott) modulate neural activity to reduce chronic pain without inducing paresthesia.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted within the epidural space to deliver the electrical pulses to the appropriate nerve tissue within the spinal cord. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

Neurostimulation system 100 of the illustrated embodiment includes a generator portion, shown as implantable pulse generator (IPG) 110, for providing a stimulation or energy source, a stimulation portion, shown as lead 130, for application of the stimulus pulse(s), and an optional external controller, shown as programmer/controller 140, to program and/or control IPG 110 via a wireless communications link. IPG 110 may be implanted within a living body (not shown) for providing electrical stimulation from IPG 110 to a selected area of the body via lead 130. In some embodiments, IPG 110 provides electrical stimulation under control of external programmer/controller 140. It should be appreciated that, although lead 130 is illustrated to provide a stimulation portion of stimulation system 100 and is configured to provide stimulation remotely with respect to the generator portion 110 of stimulation system 100, a lead 130 as described herein is intended to encompass a variety of stimulation portion configurations. For example, lead 130 may comprise a microstimulator electrode disposed adjacent to a generator portion. Furthermore, a lead configuration may include more (e.g., 8, 16, 32, etc.) or fewer (e.g., 1, 2, etc.) electrodes than those represented in the illustrations.

IPG 110 of the illustrated embodiment includes power supply 111, voltage regulator 113, RF circuitry 114, microcontroller (or microprocessor) 115, output driver circuitry 116, and clock 117, as are described in further detail below. Power supply 111 provides a source of power, such as from battery 112, to other components of IPG 110, as may be regulated by voltage regulator 113. Battery 112 may comprise a non-rechargeable (e.g., single use) battery, a rechargeable battery, a capacitor, and/or like power sources. Fuel gauge 118 monitors the life of battery 112 in some embodiments. In some embodiments, the entire IPG 110 device may need to be accessed by a surgical procedure to replace battery 112. In other embodiments, when battery 112 is depleted, it may be recharged while still within a patient's body using, for example, inductive coupling and external charging circuits. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

RF circuitry 114 provides data communication between microcontroller 115 and controller 142 in external programmer/controller 140, via transmitter 141. It should be appreciated that RF circuitry 114 may be a receiver, a transmitter, and/or transceiver depending upon the communication links desired using far-field and/or near field communication communications. The communication links may be established using suitable communication methods such as inductive wireless communication, low energy BLUETOOTH® communication, and medical band wireless communication as examples. An example of BLUETOOTH® communication between an implantable medical device and a programmer device is found, for example, in U.S. Pat. No. 9,894,691, entitled SYSTEMS AND METHODS FOR ESTABLISHING A COMMUNICATION LINK BETWEEN AN IMPLANTABLE MEDICAL DEVICE AND AN EXTERNAL INSTRUMENT, the disclosure of which is incorporated herein by reference.

Microcontroller 115 provides control with respect to the operation of IPG 110, such as in accordance with a program provided thereto by external programmer/controller 140. Software code is typically stored in memory (not shown) of IPG 110 for execution by the microcontroller 115 to control the various components of the device. The software code stored in memory of IPG 110 may support operations of embodiments disclosed herein.

Output driver circuitry 116 generates and delivers pulses to selected ones of electrodes 132-135 on lead body 131 under control of microcontroller 115. For example, voltage multiplier 151 and voltage/current control 152 may be controlled to deliver a constant current pulse of a desired magnitude, duration, and frequency to a load present with respect to selected ones of electrodes 132-135. Clock 117 preferably provides system timing information, such as may be used by microcontroller 115 in controlling system operation, as may be used by voltage multiplier 151 in generating a desired voltage, etcetera.

Lead 130 of the illustrated embodiment includes lead body 131, preferably incorporating a plurality of internal conductors coupled to lead connectors (not shown) to interface with lead connectors 153 of IPG 110. Lead 130 further includes electrodes 132-135, which are preferably coupled to the internal conductors 153. The internal conductors provide electrical connection from individual lead connectors to each of a corresponding one of electrodes 132-235. In the exemplary embodiment the lead 130 is generally configured to transmit one or more electrical signals from IPG 110 for application at, or proximate to, a spinal nerve or peripheral nerve, brain matter, muscle, or other tissue via electrodes 132-135. IPG 110 is capable of controlling the electrical signals by varying signal parameters, such as intensity, duration and/or frequency in order to deliver a desired therapy or otherwise provide operation as described herein.

Although the embodiment illustrated in FIG. 1 includes four electrodes, it should be appreciated that any number of electrodes, and corresponding conductors, may be utilized according to some embodiments. Moreover, various types, configurations and shapes of electrodes (and lead connectors) may be used according to some embodiments. An optional lumen (not shown) may extend through the lead 130, such as for use in delivery of chemicals or drugs or to accept a stylet during placement of the lead within the body. Additionally, or alternatively, the lead 130 (stimulation portion) and IPG 110 (generator portion) of stimulation system 100 may comprise a unitary construction, such as that of a microstimulator configuration.

As mentioned above, programmer/controller 140 provides data communication with IPG 110, such as to provide control (e.g., adjust stimulation settings), provide programming (e.g., after the electrodes to which stimulation pulses are delivered), etc. Accordingly, programmer/controller 140 of the illustrated embodiment includes transmitter 141 for establishing a wireless link with IPG 110, and controller 142 to provide control with respect to IPG 110. Programmer/controller 140 may receive data from IPG 110 indicating battery life or usage, such as, for example, data from fuel gauge 118 that can be displayed to medical personnel or a clinician on a screen (not shown) on programmer/controller 140. Additionally, or alternatively, programmer/controller 140 may provide power to IPG 110, such as via RE transmission by transmitter 141. Optionally, however, a separate power controller may be provided for charging the power source 111 within IPG 110.

Additional detail with respect to pulse generation systems and the delivery of stimulation pulses may be found in U.S. Pat. No. 6,609,031, entitled "MULTIPROGRAMMABLE TISSUE STIMULATOR AND METHOD" the disclosure of which is hereby incorporated herein by reference. Similarly, additional detail with respect to pulse generation systems and the delivery of stimulation pulses may be found in U.S. Pat. No. 7,937,158, entitled "MULTIPROGRAMMABLE TRIAL STIMULATOR."

Having generally described stimulation system 100 above, the discussion which follows provides detail with respect to various functional aspects of stimulation system 100 according to some embodiments. Although the below embodiments are described with reference to stimulation system 100, and IPG 110 thereof, it should be appreciated that the inventive concepts described herein are not limited to application to the exemplary system and may be used in a wide variety of medical devices.

A critical feature in implantable battery-powered systems, such as stimulation system 100, is the ability to monitor charge taken from the battery over time. This can be accomplished using measurements of the battery voltage, but accuracy of this method is limited as there are portions of a battery's voltage versus capacity curve that have a rather flat slope so that a very small change in voltage can indicate a large drop in capacity. A common method of solving the charge-monitoring problem and improving accuracy is with a fuel gauge that monitors system current draw. In this case, the voltage across a small series sense resistor is measured and converted into a frequency that is proportional to system current draw. The measurement circuit connects to a counter and increments the counter every time a specified amount of charge is delivered.

The challenge with this type of fuel gauge is that any offset in the measurement circuit can be difficult to remove through calibration because it is a shift in frequency and not simply a voltage that can be subtracted. This issue is exacerbated by the very small signals being measured as the sense resistor value must be kept low to not impact system headroom. Chopper stabilization or correlated double sampling can reduce the DC offset, but those methods require increased current draw and high frequency clocks which is undesirable in a battery-powered implantable system.

The embodiments disclosed herein create an ultra-low-power fuel gauge option in which measurement offset is not a factor. An offset-free ultra-low-power fuel gauge can be accomplished by controlling charge delivery instead of monitoring sense resistor voltages. Instead of delivering charge to the system directly from the battery, the fuel gauge delivers charge in controlled packets to the system from a large capacitor. A specific amount of charge is delivered when this large capacitor (e.g., 10 µF or more) is discharged by a programmable change in voltage (ΔV). The charge delivered can be easily represented as:

$$Q = C * \Delta V \tag{Eq. 1}$$

where C is the value of the external capacitor and ΔV is change in voltage across the capacitor. To represent the charge delivered to the system, a counter accumulates how many times this fixed amount of charge is delivered.

Figure 2:
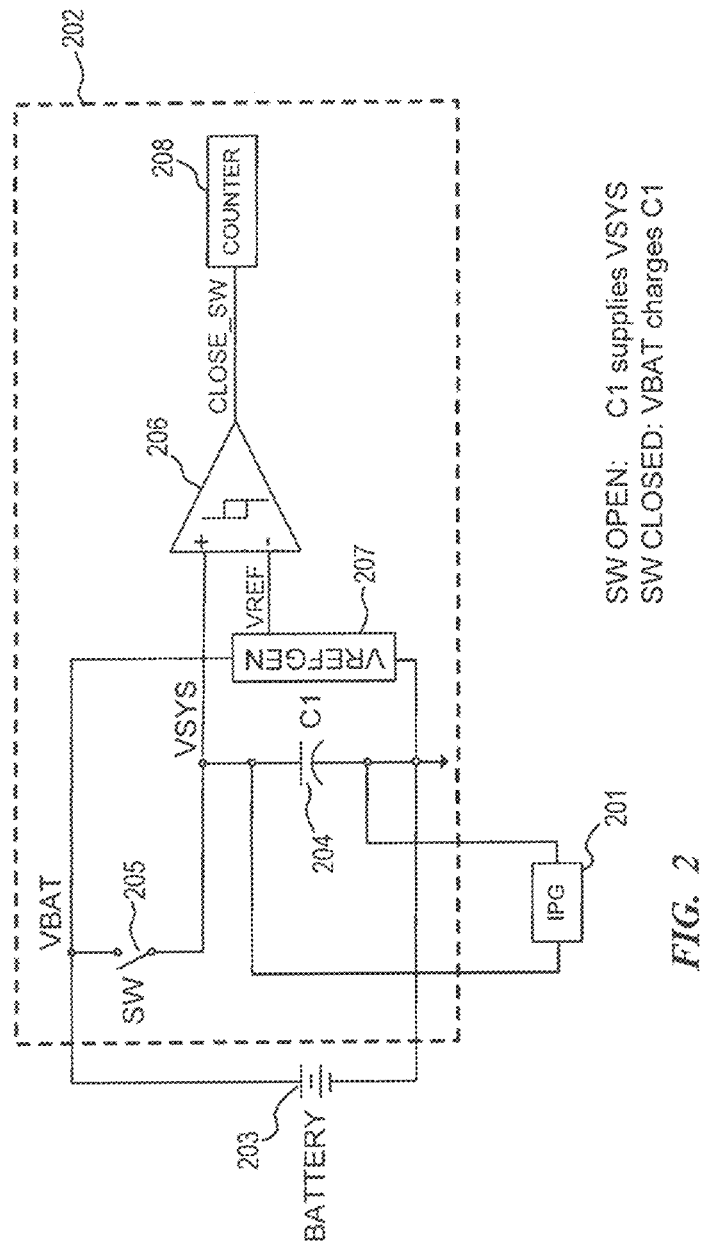
FIG. 2 depicts an ultra-low-power fuel gauge for a stimulation system according to an example embodiment using a single capacitor.

FIG. 2 depicts an ultra-low-power fuel gauge for a stimulation system according to an example embodiment using a single capacitor. A stimulation system, such as IPG 201, is powered by battery 203 through fuel gauge 202. Battery 203 provides a voltage VBAT to the fuel gauge 202. IPG 201 is connected to capacitor (C1) 204, which provides voltage VSYS. When switch (SW) 205 is closed, battery 203 charges capacitor 204 to voltage VBAT. When switch 205 is open, capacitor 204 alone provides voltage VSYS, which drops over time from the original value VBAT as the charge on capacitor 204 is provided to IPG 201. A comparator 206 monitors the VSYS voltage and compares it to a programmed reference voltage (VREF) from reference voltage generator VREFGEN 207. When the VSYS voltage drops to at or below VREF, the output of comparator 206 asserts (CLOSE_SW) and causes capacitor 204 to be returned to the charging state by closing switch 205. Switch 205 may remain closed for a predetermined interval to allow capacitor 204 to recharge. The duration of the interval may be selected based upon the size of capacitor 204, the voltage VBAT from battery 203, and the voltage droop allowed by VREFGEN. When switch 205 is closed, IPG 201 is briefly powered by battery 203 while capacitor 204 recharges.

The output of comparator 206 also increments counter 208. Each count by counter 208 represents a packet of charge that has been delivered to IPG 201 from capacitor 204. Counter 208 may be, for example, a register, state machine, or other accumulator circuit. The output of comparator 206 may be defined as Charge/Count (e.g., µC/Count). Instead of measuring a very small voltage signal across a series sense resistor as used in prior charge-monitoring systems, fuel gauge 202 delivers charge in pre-determined packets. Referring to Equation 1 above, the size of the charge packets can be defined by the value (C) of capacitor 204 and the amount of voltage droop (ΔV) allowed on VSYS, which is set by VREFGEN (e.g., the drop from VBAT to VREF). The only circuit that contributes offset is comparator 206 itself; however, that offset will only affect the ΔV allowed per cycle, which can be calibrated out when determining the actual Charge/Count. The offset also depends on the value of capacitor 204, so the offset is naturally removed as part of the capacitor calibration. Clocked circuits are not needed for operation of the fuel gauge or for offset correction. This ensures that the power consumption is minimal and suitable to implantable battery-powered products. The value of counter 208 can be transmitted periodically or on demand to an external programmer/controller, such as programmer/controller 140 (FIG. 1), which may then calculate a total charge provided from battery 203 and an estimated remaining lifetime and/or voltage for battery 203.

Figure 3:
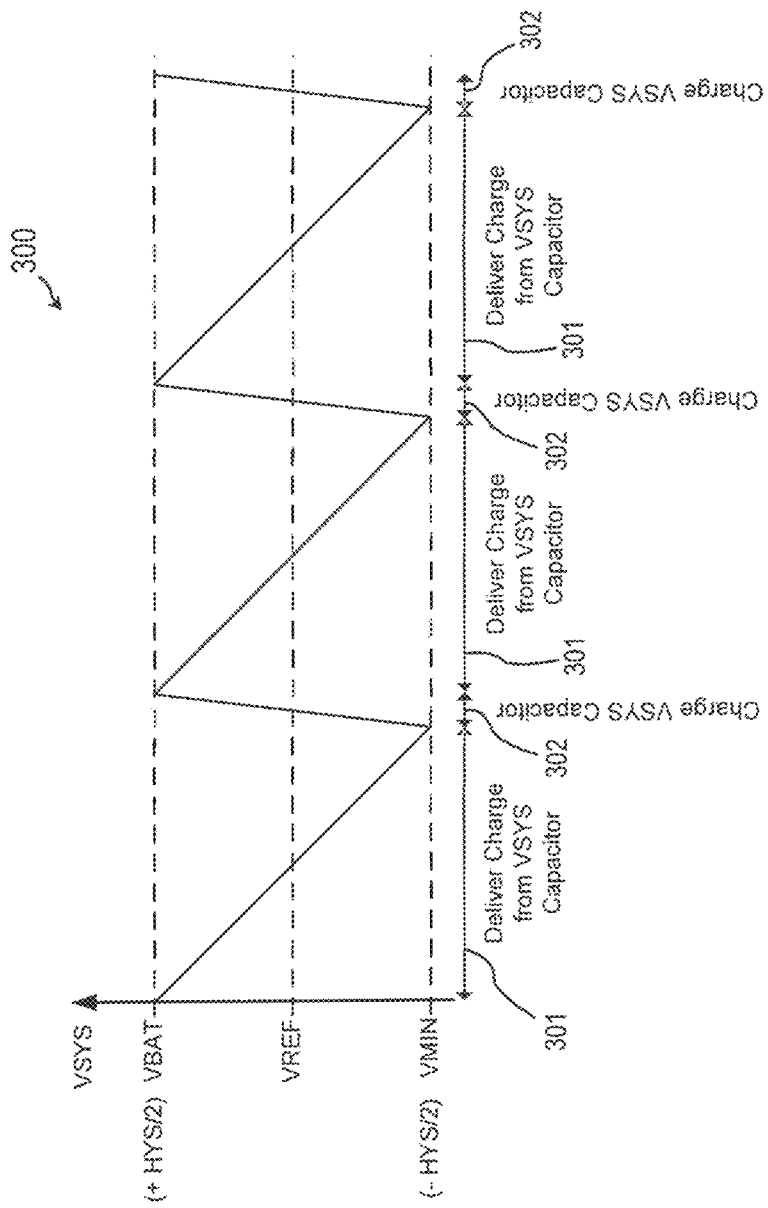
FIG. 3 is a graph illustrating the change in voltage VSYS by a single fuel gauge capacitor in one embodiment.

FIG. 3 is a graph 300 illustrating the change in voltage VSYS across capacitor 204 (FIG. 2) in an embodiment. During intervals 301, capacitor 204 alone is delivering charge to IPG 201 (i.e., switch 205 is open) and the voltage VSYS across the capacitor drops from a fully charged voltage VBAT to a minimum voltage VMIN. When VSYS drops to VMIN, interval 301 ends and capacitor 204 is recharged during interval 302 back to voltage VBAT. During interval 302, the voltage VSYS provided to IP G 201 increases from VMIN back to VBAT while capacitor 204 is recharging. Interval 302 ends when capacitor 204 is charged to VBAT, and then a new supply interval 301 begins. Hysteresis (HYS) in the system can be set in an embodiment by comparator 206 and the reference voltage VREF from VREFGEN 207. VREF is a programmable trip point that controls the supply/recharge cycle by triggering the closing of switch 205 so that capacitor 204 can recharge.

Figure 4:
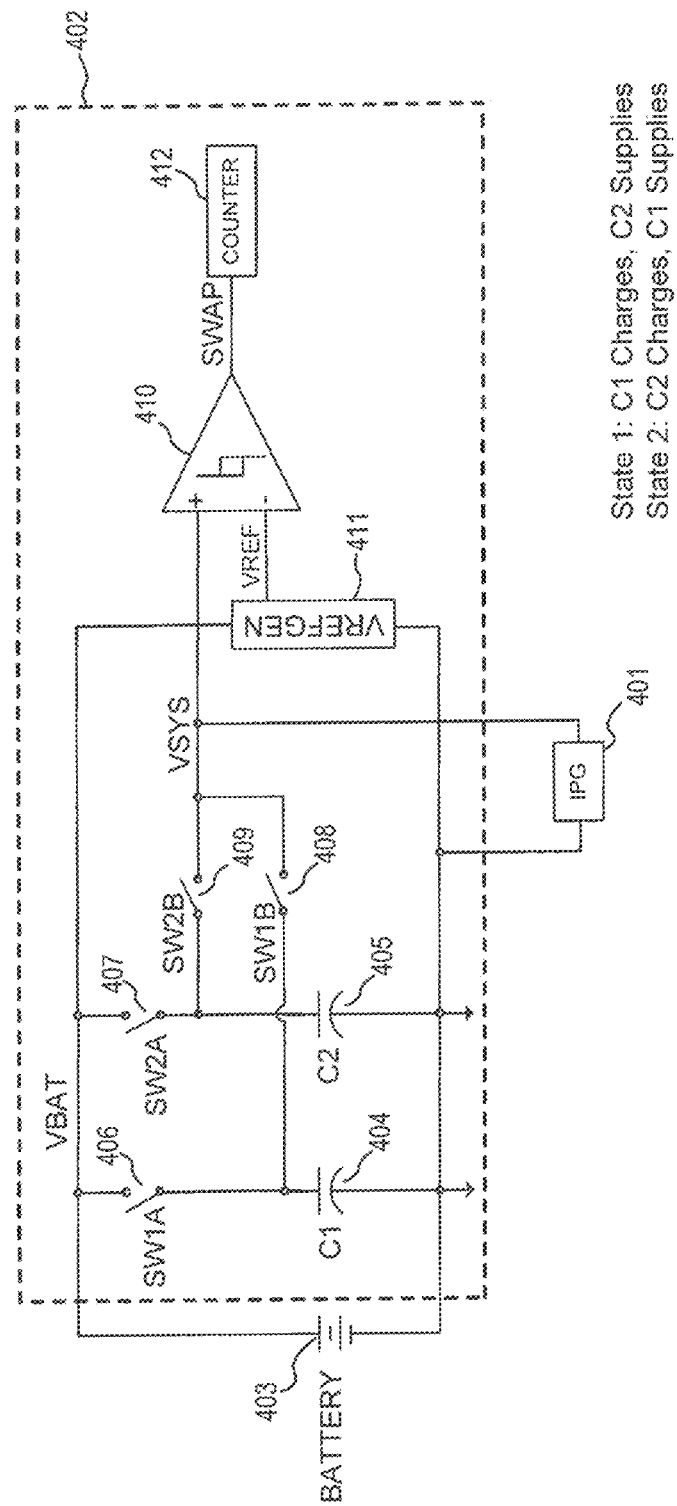
FIG. 4 depicts an ultra-low-power fuel gauge for a stimulation system according to an example embodiment using a dual capacitor configuration.

FIG. 4 depicts an ultra-low-power fuel gauge for a stimulation system according to an example embodiment using a dual capacitor configuration. A stimulation system, such as IPG 401, is powered by fuel gauge 402. Battery 403 provides a voltage VBAT to the fuel gauge 402. IPG 201 is connected to capacitors (C1) 404 and (C2) 405 in fuel gauge 402, which provide voltage VSYS to IPG 401. In this embodiment, the two capacitors (C1) 404 and (C2) 405 are independently coupled to battery 403 through charging switches (SW1A) 406 and (SW2A) 407, respectively. When charging switch 406 is closed, battery 403 charges capacitor 404 to voltage VBAT. When charging switch 407 is closed, battery 203 charges capacitor 405 to voltage VBAT. Capacitors 404 and 405 are independently coupled to IPG 401 through supply switches (SW1B) 408 and (SW2B) 409, respectively. When supply switch 408 is closed, capacitor 404 is coupled to IPG 401 and provides voltage VSYS. When supply switch 409 is closed, capacitor 405 is coupled to IPG 401 and provides voltage VSYS. In an embodiment, only one charging switch 406 or 407 is closed at any time, and only one supply switch 408 or 409 is closed at any time. In a further embodiment, the switches (406/408 or 407/409) associated with each capacitor 404 and 405 are not both closed at the same time.

In an embodiment, fuel gauge 402 has two operating states. In a first state, capacitor 404 is charged by battery 403 to voltage VBAT, and capacitor 405 supplies charge to IPG 401 at voltage VSYS. The first state may be selected, for example, by closing switches 406 and 409 and opening switches 407 and 408. Once charged, capacitor 404 may hold voltage VBAT with switch 406 either open or closed. In a second state, capacitor 405 is charged by battery 403 to voltage VBAT, and capacitor 404 supplies charge to IPG 401 at voltage VSYS. The second state may be selected, for example, by opening switches 406 and 409 and closing switches 407 and 408. Once charged, capacitor 405 may hold voltage VBAT with switch 407 either open or closed.

The selected supply capacitor 404 or 405 for a current state provides voltage VSYS to IPG 401. The voltage VSYS drops over time from the initial value VBAT as charge is provided to IPG 401 from the supply capacitor 404 or 405. A comparator 410 monitors the VSYS voltage value from the selected capacitor and compares it to a programmed reference voltage (VREF) from VREFGEN 411. When the VSYS voltage drops to at or below the programmed reference from VREFGEN 411, the output of comparator 410 asserts (SWAP) and causes the fuel gauge 402 to change states. The state is changed by selecting the appropriate positions of switches 406-409 so that the current charging or fully charged capacitor begins to supply VSYS to IPG 401 and the current supply capacitor begins charging. The selected charging switch 406 or 407 may remain closed for a predetermined interval to allow the respective capacitor 404 or 405 to recharge to VBAT. The duration of the interval may be selected based upon the size of capacitor 404, 405, the voltage VBAT from battery 403, and the voltage droop allowed by VREFGEN. Once the charging capacitor is charged to VBAT, the respective charging switch 406 or 407 may remain closed or may be opened.

The output of comparator 410 also increments counter 412. Each count by counter 412 represents a packet of charge that has been delivered to IPG 401 from capacitor 404 or 405. The output of counter 412 may be defined as Charge/Count (e.g., µC/Count). Similar to fuel gauge 202 discussed above, fuel gauge 402 delivers charge in predetermined packets. The size of the packets is defined by the value of capacitors (C1) 404 and (C2) 405 and the amount of voltage droop (ΔV) allowed on VSYS, which is set by VREFGEN (e.g., the drop from VBAT to VREF). The value of counter 412 may be transmitted periodically or on demand to an external programmer/controller, such as programmer/controller 140 (FIG. 1), which may then calculate a total charge provided from battery 403 and an estimated remaining lifetime and/or voltage for battery 403.

Although the embodiment illustrated in FIG. 4 uses two capacitors, it will be understood that other embodiments may use three or more capacitors. Additional capacitors (Cx, not shown) may be added in parallel to capacitors (C1) 404 and (C2) 405. Each additional capacitor (Cx) would have its own charging switch (SWxA, not shown) and supply switch (SWxB, not shown), respectively. In such an embodiment, the output of comparator 410 (SWAP) causes the fuel gauge to sequentially select each capacitor by selecting the appropriate positions of the respective charging and supply switches for each capacitor.

Figure 5:
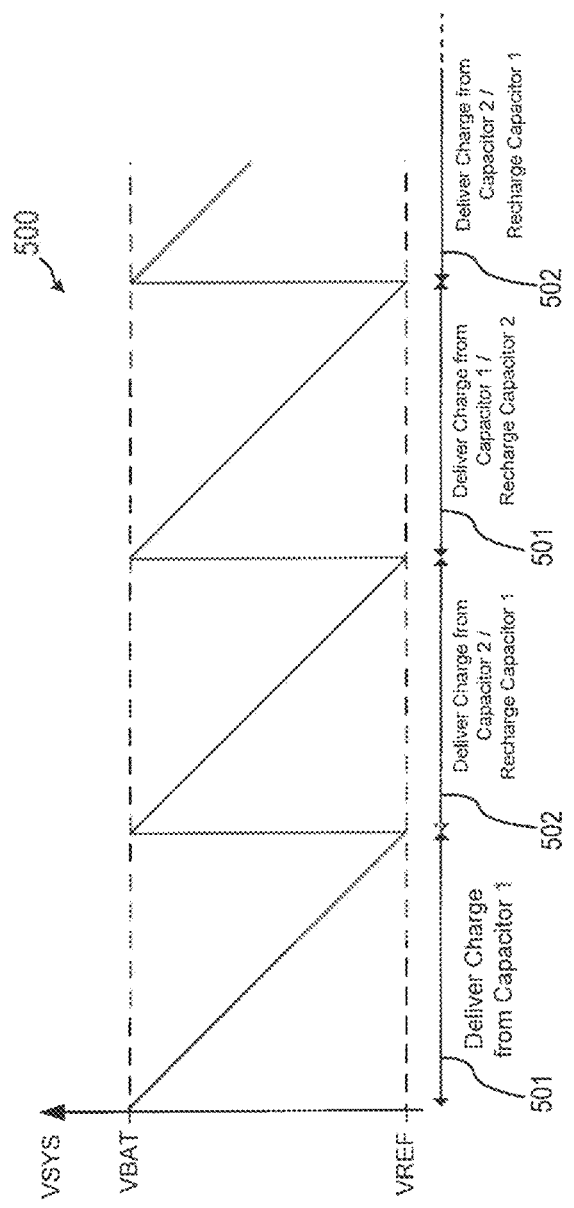
FIG. 5 is a graph illustrating the change in voltage VSYS that is suppled to an implanted device by a fuel gauge with two capacitors in one embodiment.

FIG. 5 is a graph 500 illustrating the change in voltage VSYS that is suppled to IPG 401 (FIG. 4) in an embodiment. During interval 501, capacitor C1 404 delivers charge to IPG 401. The voltage VSYS across capacitor 404 drops from fully charged voltage VBAT to the reference voltage VREF during interval 501. When VSYS drops to VREF, interval 501 ends and fuel gauge 402 selects capacitor C2 405 during interval 502 to deliver charge to IPG 401. Capacitor 404 is recharged back to voltage VBAT during interval 502. When the voltage VSYS across capacitor 405 drops from fully charged voltage VBAT to the reference voltage VREF, interval 502 ends and a new interval 501 begins again. Fuel gauge 402 cycles between intervals 501 and 502 while switching between capacitors 404 and 405 to power IPG 402. Because there is no need to wait for a depleted capacitor to charge in the dual-capacitor configuration, the supply voltage VSYS jumps from VREF to VBAT each time a new interval 501 or 502 begins and a new capacitor is switched to supply IPG 402.

Although FIGS. 4 and 5 illustrate a charge delivery fuel gauge having two capacitors, it will be understood that in other embodiments a fuel gauge may have any number of capacitors. The number of capacitors used in the fuel gauge depends on the current draw of the system being supplied. For example, additional capacitors (not shown) may be added to fuel gauge 402 using additional supply and charging switches (not shown). Each assertion of the SWAP command from comparator 410 may be used to select a next capacitor sequentially from a group of three or more capacitors in such a configuration. For low currents, only a single capacitor is required, as illustrated in FIG. 1, but the number of capacitors can be increased for higher system currents.

FIG. 3 illustrates that there is a small amount of time (302) during which the system current is not being monitored when using a single capacitor. This time may cause errors to accumulate at higher current levels. At low currents, this error is tolerable; however, additional capacitors may be used to eliminate the error at higher currents. In single-capacitor mode (FIG. 2), comparator 206 hysteresis sets ΔV. In the dual-capacitor mode (FIG. 4), one capacitor is charged in the background while the other is powering the system. This eliminates the error due to the recharge interval (302) and allows monitoring of higher current systems. In the dual-capacitor mode, ΔV is set by the reference voltage. The number of capacitors can be expanded further to support higher current draw.

Figure 6:
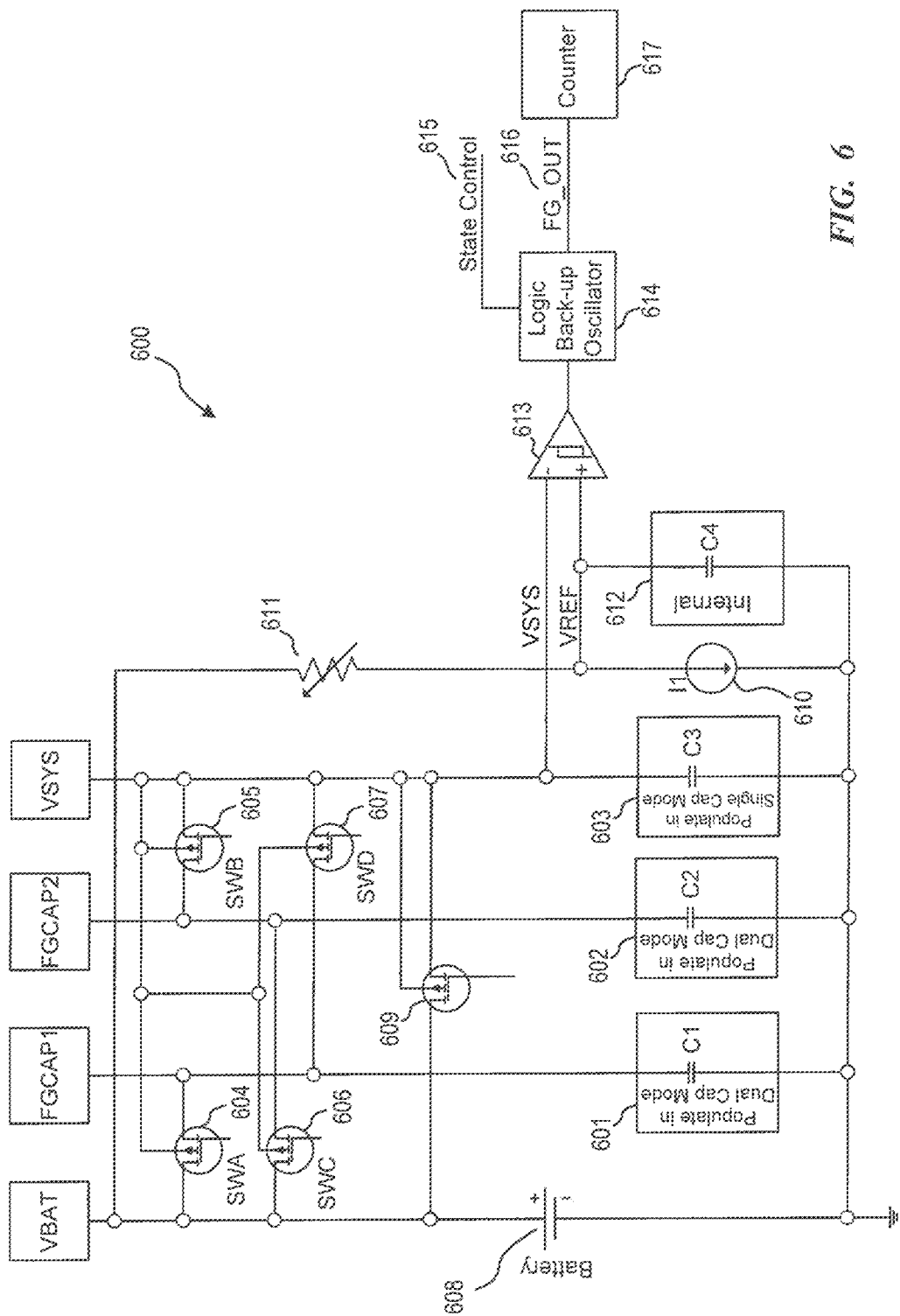
FIG. 6 depicts a configurable charge delivery fuel gauge circuit according to one embodiment.

FIG. 6 depicts a configurable version of a charge delivery fuel gauge 600 according to one embodiment. Fuel gauge 600 can be configured for operation in either single-capacitor mode or dual-capacitor mode depending on how capacitors 601-603 are populated. For single-capacitor mode, only capacitor (C3) 603 needs to be populated. In this configuration, capacitors (C1) 601 and (C2) 602 are not populated, and the respective branches of fuel gauge 600 are open circuits that can be ignored. For dual-capacitor mode, capacitors (C1) 601 and (C2) 602 are populated, but capacitor (C3) 603 is not populated. In this configuration, the C3 branch of fuel gauge 600 is an open circuit that can be ignored.

In either configuration, switches 604-607 are selected as appropriate to couple capacitors 601 and 602 to either battery 608 for recharging or to the VSYS output to power an IPG or other component in dual-capacitor mode. Switches 604 and 607 control the charging and supply connections for capacitor 601, and switches 605 and 606 control the charging and supply connections for capacitor 602. Switch 609 may be selected as appropriate to couple capacitor 603 to battery 608 for recharging in single-capacitor mode. Current source 610, variable resistor 611, and capacitor (C4) 612 function as a reference voltage generator to set voltage VREF. Comparator 613 receives VSYS and VREF as inputs. Comparator 613 monitors the VSYS voltage value from the selected capacitor and compares it to the programmed reference voltage (VREF). When the VSYS voltage drops to at or below the reference voltage, the output of comparator 613 drives logic back-up oscillator 614, which outputs state control signal 615 and fuel gauge output (FG_OUT) 616. State control 615 is used to control switches 604-609 to change capacitor states between supply and charging. Fuel gauge output 616 increments counter 617. Each count by counter 617 represents a packet of charge that has been delivered by fuel gauge 600. The output of counter 617 may be defined as Charge/Count (e.g., μC/Count). The size of the packets is defined by the value of capacitors 601-603 and the amount of voltage droop (ΔV) allowed on VSYS (e.g., the drop from VBAT to VREF). The value of counter 617 may be transmitted periodically or on demand to an external programmer/controller, such as programmer/controller 140 (FIG. 1), which may then calculate a total charge provided from battery 608 and an estimated remaining lifetime and/or voltage for battery 608.

In an embodiment, most of the components in fuel gauge 600 (e.g., switches 604-609, current source 610, resistor 611, comparator 613, and oscillator 614 may be constructed as a single chip. Capacitors 601-603 may be off-chip components that are selected based upon desired operating parameters.

Figure 7A:
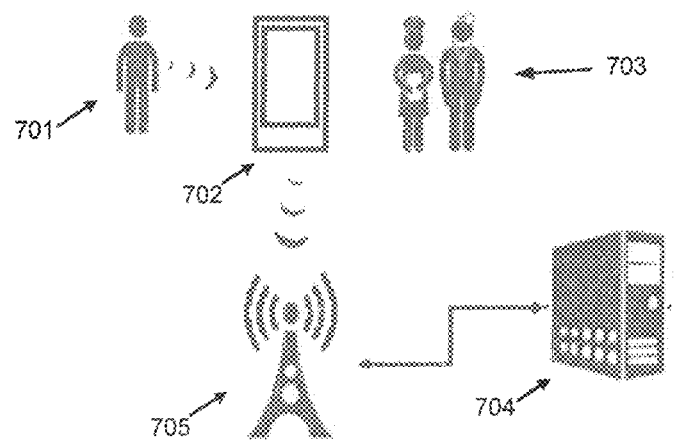
FIG. 7A depicts a system in which an implanted medical device provides battery life data to a programmer device according to some representative embodiments.

FIG. 7A depicts a system in which an implanted medical device provides battery life data to a programmer device according to some representative embodiments. The implanted medical device (not shown in FIG. 7) is implanted within patient 701. Examples of suitable implantable medical devices include neurostimulators such as the Protege Prodigy™, Proclaim™, Infinity™ pulse generators available from Abbott (Plano, Tex.). Also, other example implantable medical devices include cardiac rhythm management devices and cardiac devices include Ellipse™ implantable Cardioverter/Defibrillator (ICDs), Fortify Assura™ ICDs, Assurity MRI™ pacemakers, and Endurity™ pacemakers available from Abbott (Sylmar, Calif.). Any suitable implantable medical device or personal medical device may operate according to embodiments described herein.

At appropriate times, the implanted medical device of patient 701 communicates with clinician programmer device 702, which is operated by one or more clinicians 703. The programming clinician 703 utilizes one or more user interface screens of device 702 to define or control a therapy provided to patient 701 by the implanted medical device. The clinician(s) may define or set one or more therapy parameters. For example, the clinician may define pulse amplitudes, pulse frequencies, pulse patterns, pacing delays, and/or a variety of other therapy parameters depending upon the implanted device and the intended therapy for patient 701.

During a programming session, programming data may be communicated from clinician programmer device 702 to one or more remote device management servers 704 via network 705. The set of programming data is subjected to authorization and validation processes to ensure that only programming data from authorized clinicians will accepted by the implanted medical device of patient 701. Suitable security algorithms may be employed to validate and authorize communication between clinician programmer device 702 and servers 704, such as communication of user/clinician identifiers, passwords, device identifiers, network identifiers, security/cryptographic keys, digital certificates, location data, and/or the like. The implanted medical device of patient 701 may also provide information, such as battery life data, to clinician programmer device 702. As disclosed herein, this battery life data may comprise, for example, a charge count representing a number of discharge cycles for capacitors in a fuel gauge of the implanted medical device of patient 701. The battery life data may be used to indicate the remaining longevity or battery voltage of the implanted medical device of patient 701 on a display of the clinician programmer device 702.

The clinician programmer device 702 may display an Elective Replacement Indicator ("ERI") to a physician or clinician. The ERI informs the physician or clinician that the device's power supply is nearing its end-of-life, which is a point at which the power supply cannot provide sufficient energy to keep the implanted device operable. The advance warning provided by an ERI gives the physician or clinician the opportunity to take the appropriate measures, such as replacing the device, prior to the power supply's end of life.

Figure 7B:
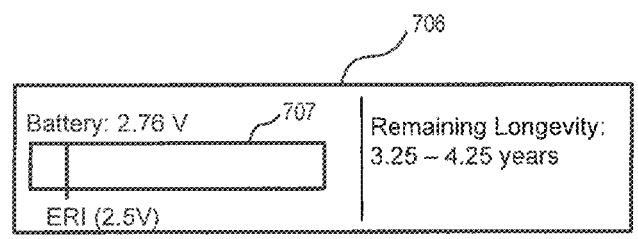
FIG. 7B depicts a battery condition display having a bar graph that may be in displayed on the clinician programmer device in an embodiment.

FIG. 7B depicts a battery condition display 706 having a bar graph 707 that may be in displayed on the clinician programmer device 702 in an embodiment. Bar graph 707 uses battery voltage as an indicator of the battery condition. In one embodiment, charge count data received form the implanted medical device of patient 701 may be used to calculate or estimate the current battery voltage for use in generating battery condition display 706 and bar graph 707.

Figure 7C:
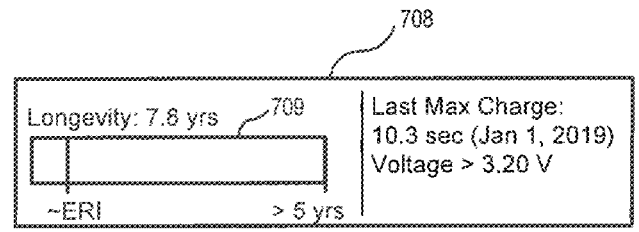
FIG. 7C depicts a battery condition display having a longevity estimate bar that may be in displayed on the clinician programmer device in an embodiment.

FIG. 7C depicts a battery condition display 708 having a longevity estimate bar 709 that may be in displayed on the clinician programmer device 702 in an embodiment. Longevity estimate bar 709 as displayed on clinician programmer device 702 may take the battery voltage into account as well as the programmed parameters, telemetry usage, and other factors affecting current battery drain in one embodiment, charge count data received form the implanted medical device of patient 701 may be used to calculate or estimate the current battery voltage for use in generating battery condition display 708 and longevity bar graph 709.

Figure 8:
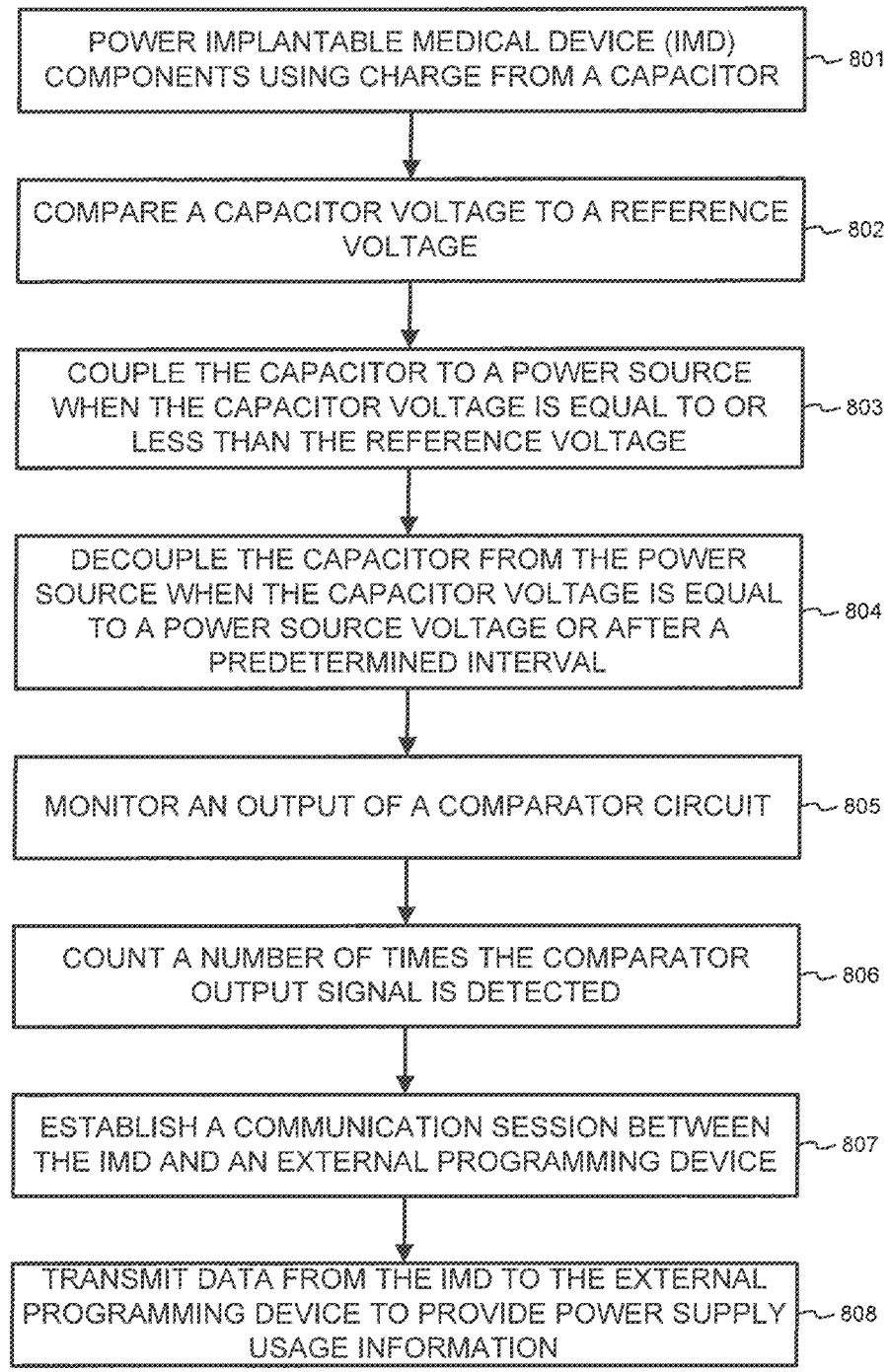
FIG. 8 depicts a flowchart illustrating a method for monitoring power usage in an implantable medical device using a single capacitor fuel gauge according to an embodiment.

FIG. 8 depicts a flowchart illustrating a method for monitoring power usage in an implantable medical device (IMD) according to an embodiment. In step 801, IMD components are powered using charge from a capacitor. In step 802, a capacitor voltage is compared to a reference voltage. The reference voltage may be created using a voltage generator circuit, for example. In step 803, the capacitor is coupled to a power source when the capacitor voltage is equal to or less than the reference voltage. For example, a switch may be used to couple the capacitor to the power source when a comparator output signal is detected. The power source is a battery in one embodiment. In step 804, the capacitor is decoupled or disconnected from the power source when the capacitor voltage is equal to a power source voltage or after a predetermined interval.

In step 805, an output of a comparator circuit is monitored. The comparator circuit may be used, for example, to compare the capacitor voltage to the reference voltage. In step 806, detections of the comparator output signal are counted. In step 807, a communication session between the IMD and an external programming device is established. In step 808, data is transmitted from the IMD to the external programming device to provide power supply usage information. The power supply usage information may comprise, for example, a count of comparator output signal detections.

Figure 9A:
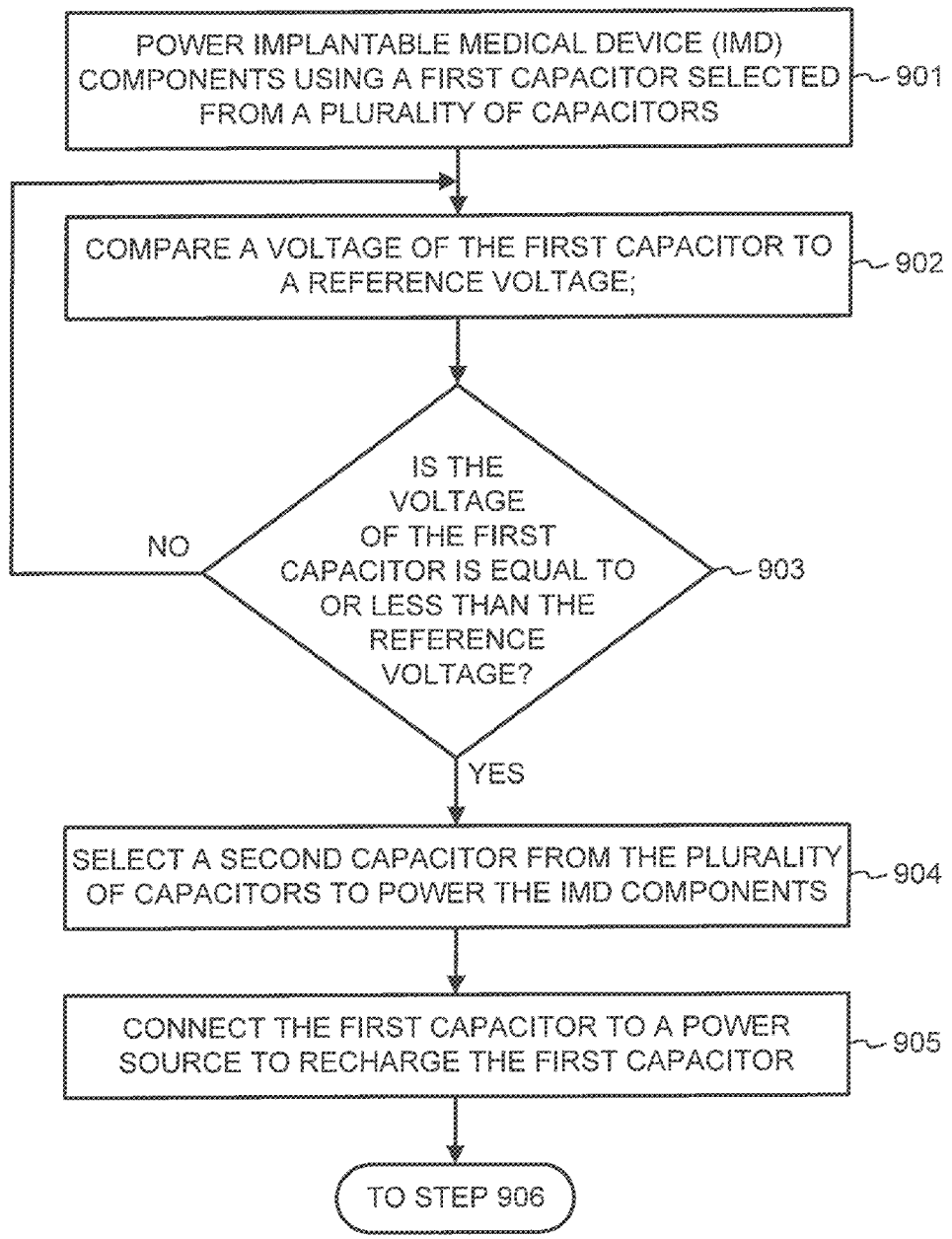
FIGS. 9A and 9B depict a flowchart illustrating a method for monitoring power usage in an implantable medical device using a fuel gauge having a plurality of capacitors according to an embodiment.
Figure 9B:
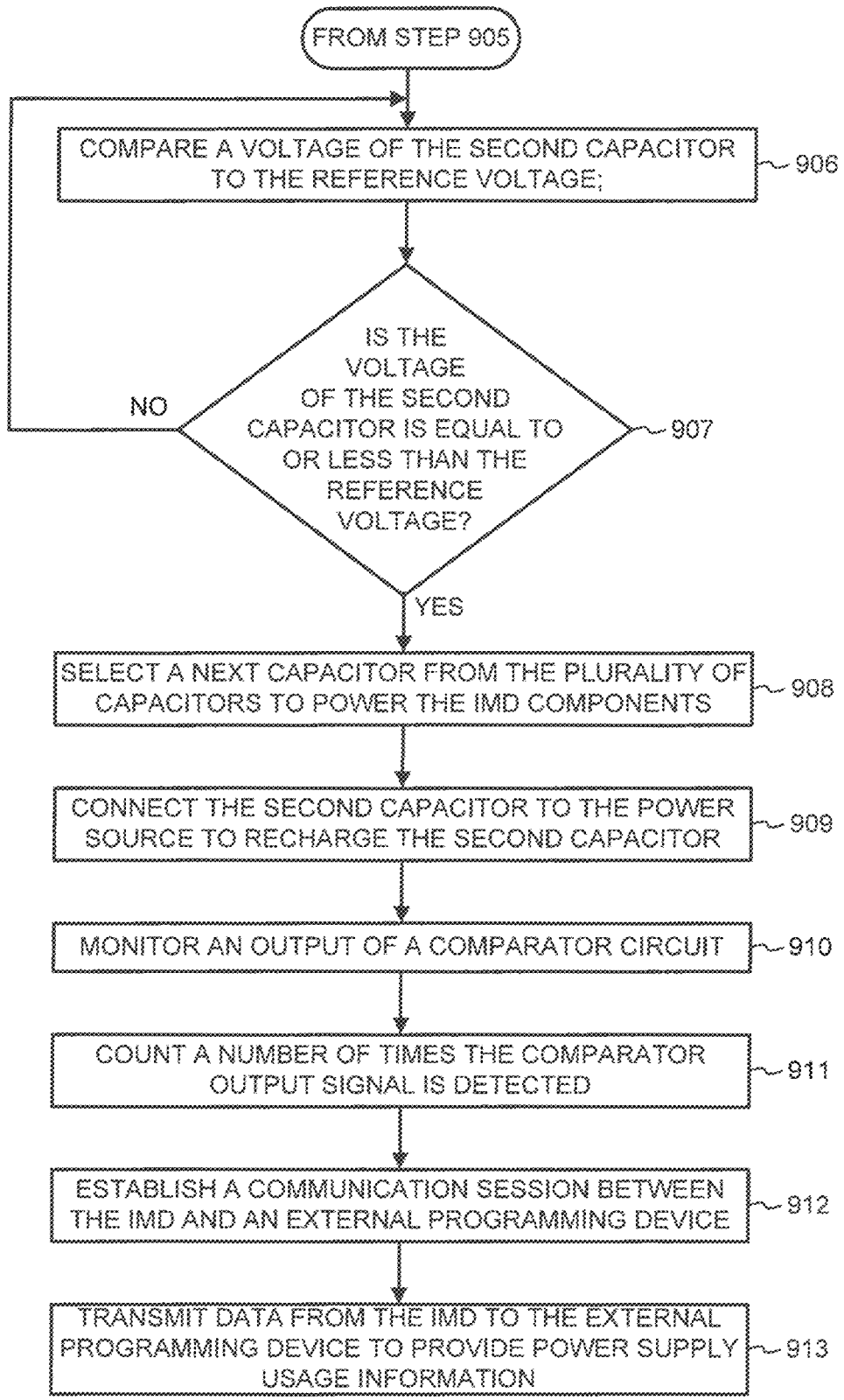

FIGS. 9A and 9B depict a flowchart illustrating a method for monitoring power usage in an implantable medical device (IMD) using a fuel gauge having a plurality of capacitors. In step 901, IMD components are powered using a first capacitor selected from a plurality of capacitors. In step 902, a voltage of the first capacitor is compared to a reference voltage. The reference voltage may be created, for example, a voltage generator circuit, such as a current source connected in series with a resistance. In step 903, the voltage of the first capacitor is evaluated to determine if it is equal to or less than the reference voltage. If the first capacitor is evaluated as higher than the reference voltage, then the process continues to make the voltage comparison in step 902, However, if the voltage of the first capacitor is equal to or less than the reference voltage, then the process moves to step 904 in which a second capacitor is selected from the plurality of capacitors to power the IMD components. In step 905, the first capacitor is connected to a power source to be recharged. The power source may be a battery, for example.

In step 906, the voltage of the second capacitor is evaluated to determine if it is equal to or less than the reference voltage. If the second capacitor is evaluated higher than the reference voltage, then the process continues to make the voltage comparison in step 906. However, if the voltage of the second capacitor is equal to or less than the reference voltage, then the process moves to step 908 in which a next capacitor is selected from the plurality of capacitors to power the IMD components. In step 909, the second capacitor is connected to the power source to be recharged.

In one embodiment, the fuel gauge comprises two capacitors, and the "next" capacitor hi step 908 is the first capacitor, and the process may repeat at step 902 (not shown). In other embodiments, the fuel gauge comprises three or more capacitors, and the "next" capacitor in step 908 is a third or other capacitor. In an embodiment, the process illustrated in steps 906-909 may be repeated any number of times to cycle sequentially through three or more capacitors (not shown). For example, the output of a comparator circuit may be monitored as part of the evaluation steps 902 and 906. If the comparator output is detected (e.g., a predetermined high or low signal or other output), then the fuel gauge alternates among a selected group of capacitors.

In step 910, an output of a comparator circuit is monitored. The comparator circuit may be used, for example, to compare the capacitor voltage to the reference voltage in steps 903 and 907. In step 911, detections of the comparator output signal are counted. In step 912, a communication session between the IMD and an external programming device is established. In step 913, data is transmitted from the IMD to the external programming device to provide power supply usage information. The power supply usage information may comprise, for example, a count of comparator output signal detections.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor based system including systems using microcontrollers, reduced instruction set computers (RISC), application specific integrated circuits (ASICs), field-programmable gate arrays (FPGAs), logic circuits, and any other circuit or processor capable of executing the functions described herein. When processor-based, the controller executes program instructions stored in memory to perform the corresponding operations. Additionally, or alternatively, the controllers and the controller device may represent circuits that may be implemented as hardware. The above examples are exemplary only and are thus not intended to limit in any way the definition and/or meaning of the term "controller."

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 § 112(f), unless and until such claim limitations expressly use the phrase "means for" followed by a statement of function void of further structure.

What is claimed is:

1. An implantable medical device (IMD), comprising:
a processor for controlling the IMD;
circuitry for providing therapeutic or diagnostic medical operations for a patient;
wireless communication circuitry for conducting wireless communications;
a non-rechargeable battery; and
device power control circuitry comprising:
  a first capacitor configured to be coupled to the non-rechargeable battery, by charging control circuitry, in a first operating state, and configured to be coupled to one or more components of the IMD, by the charging control circuitry, in a second operating state;
  a second capacitor configured to be coupled to the non-rechargeable battery, by the charging control circuitry, in the second operating state, and configured to be coupled to the one or more components of the IMD, by the charging control circuitry, in the first operating state, wherein:
    during the first operating state, the first capacitor is configured to be charged by the non-rechargeable battery while the second capacitor is configured to provide a supply voltage to the one or more components of the IMD to provide power to the IMD for therapeutic operations and non-therapeutic operations, and
    during the second operating state the second capacitor is configured to be charged by the non-rechargeable battery while the first capacitor is configured to provide the supply voltage to the one or more components of the IMD to provide the power to the IMD for the therapeutic operations and the non-therapeutic operations; and
a comparator configured to:
  receive the supply voltage from the first capacitor during the second operating state or from the second capacitor during the first operating state,
  compare the supply voltage against a reference voltage value,
    in response to the supply voltage failing to satisfy the reference voltage value, generate an output signal configured to cause a transition from the first operating state to the second operating state or from the second operating state to the first operating state, and
    increment a count value of a counter coupled to the comparator, wherein the count value corresponds to a number of times of discharge of the first capacitor, the second capacitor, or both, and an amount of charge remaining in the non-rechargeable battery is determined based on the count value.

2. The IMD of claim 1, further comprising:
a memory for storing data and executable instructions, wherein the executable instructions comprise code for causing the processor to:
(1) monitor an output of the comparator, and
(2) generate a control signal based on the output signal, wherein the control signal is configured to toggle switches of the charging control circuitry to switch from the first operating state or the second operating state to the other of the first operating state or the second operating state.

3. The IMD of claim 1, further comprising:
a memory for storing data and executable instructions, wherein the executable instructions comprise code for causing the processor to:
(a) conduct a communication session between the IMD and an external programming device, and
(b) transmit count value data from the IMD to the external programming device, wherein the count value data corresponds to the count value, and wherein the external programming device is configured to determine a remaining life of the non-rechargeable battery based on the count value data.

4. The IMD of claim 1 wherein the non-therapeutic operations comprise wireless communication operations, Bluetooth® communication operations, or both.

5. The IMD of claim 1, wherein the one or more components of the IMD include an implantable pulse generator (IPG), and wherein the therapeutic operations comprise provision of electrical stimulation to tissue of a patient via the IPG.

6. The IMD of claim 1, wherein each count value corresponds to a unit of charge provided by discharge of the first capacitor or of the second capacitor, and wherein the processor is configured to cause the wireless communication circuitry to provide count value data corresponding to a total count value of the counter to an external programmer periodically or in response to a command received from the external programmer.

7. The IMD of claim 6, wherein a remaining lifetime of the non-rechargeable battery is determined based on the count value data, wherein the non-therapeutic operations comprise the wireless communications performed by the wireless communications circuitry, and wherein the therapeutic operations comprise delivery of electrical stimulation to tissue of a patient via an implantable pulse generator (IPG) of the IMD.

8. The IMD of claim 1, further comprising a plurality of capacitors that include the first capacitor and the second capacitor, wherein the device power control circuitry is further configured to couple capacitors, in addition to the first capacitor and the second capacitor of the plurality of capacitors, to the non-rechargeable battery or to the one or more components of the IMD in a first operating state or in a second operating state.

9. The IMD of claim 1, wherein the first operating state occurs during a first time interval, and wherein the second operating state occurs during a second time interval distinct from the first time interval.

10. A method of operating an implantable medical device (IMD), the method comprising:
 operating power control circuitry of the IMD to power therapeutic and non-therapeutic operations of the IMD, wherein operating the power control circuitry comprises:
  (1) in a first operating state occurring during a first time interval, switchably coupling a non-rechargeable battery of the IMD to at least a first capacitor to charge the at least the first capacitor while switchably coupling at least a second capacitor to one or more components of the IMD to provide a supply voltage to the one or more components via discharge of the at least the second capacitor, wherein the supply voltage is configured to provide power to perform therapeutic operations and non-therapeutic operations, and
  (2) in a second operating state occurring during a second time interval distinct from the first time interval, switchably coupling the at least the first capacitor to the one or more components of the IMD to provide the supply voltage to the one or more components via discharge of the at least the first capacitor while switchably coupling the at least the second capacitor to the rechargeable battery to charge the at least the second capacitor;
 incrementing a counter to record count data related to a number of times that the at least the first capacitor and the at least the second capacitor have been discharged;
 conducting a communication session with a device external to a patient using wireless communication circuitry of the IMD; and
 communicating the count data to the device external to the patient, wherein the device external to the patient is configured to determine a remaining life of the non-rechargeable battery based on the count data.

11. The method of claim 10, further comprising:
 comparing a capacitor voltage of the at least the first capacitor or of the at least the second capacitor to a reference voltage value;
 coupling the at least the first capacitor or the at least the second capacitor to the non-rechargeable battery when the capacitor voltage fails to satisfy the reference voltage value;
 decoupling the at least the first capacitor or the at least the second capacitor from the non-rechargeable battery when the capacitor voltage satisfies a power source voltage level or after a predetermined time interval;
 monitoring an output of a comparator circuit indicating that the at least the first capacitor or the at least the second capacitor fails to satisfy the reference voltage value; and
 closing a switch to couple the at least the first capacitor or the at least the second capacitor to the non-rechargeable battery when a comparator output signal is detected.

12. The method of claim 11, further comprising:
 monitoring an output of a comparator circuit; and
 counting a number of times the comparator output signal is detected.

13. The method of claim 12, wherein the count data comprises a count of comparator output signal detections.

14. An implantable medical device (IMD), comprising:
 a processor for controlling the IMD;
 circuitry for providing therapeutic or diagnostic medical operations for a patient;
 wireless communication circuitry for conducting wireless communications;
 a non-rechargeable battery; and
 device power control circuitry comprising:
  a plurality of capacitors;
  charging control circuitry for switching between charging two or more capacitors of the plurality of capacitors using the non-rechargeable battery and discharging the two or more of the plurality of capacitors to provide power for device operations that include therapeutic operations and non-therapeutic operations, wherein switching between charging the two or more capacitors comprises:
   charging a first capacitor of the two or more capacitors by the non-rechargeable battery while a second capacitor of the two or more capacitors is configured to provide a supply voltage to one or more components of the IMD to provide power to the IMD for the therapeutic operations and the non-therapeutic operations, and
   charging the second capacitor of the two or more capacitors by the non-rechargeable battery while the first capacitor of the two or more capacitors is configured to provide the supply voltage to the one or more components of the IMD to provide power to the IMD for the therapeutic operations and the non-therapeutic operations;
  wherein the IMD is configured to maintain a count related to a number of times of discharge of the plurality of capacitors to provide an end-of-life estimation for the non-rechargeable battery.

15. The IMD of claim 14 further comprising:
 a comparator having a first input alternately coupled to a capacitor of the plurality of capacitors and having a second input coupled to a reference voltage, the comparator configured to generate an output signal when a first input voltage fails to satisfy the reference voltage, wherein the output signal is configured to swap which capacitor of the plurality of capacitors is coupled to the non-rechargeable battery and which capacitor of the plurality of capacitors is discharged to power operations of the IMD.

16. The IMD of claim 15, wherein, in response to the output signal, at least a first capacitor of the plurality of capacitors or at least a second capacitor of the plurality of capacitors is coupled to the non-rechargeable battery for a predetermined time interval and is decoupled from the non-rechargeable battery after the predetermined time interval.

17. The IMD of claim 15, wherein, in response to the output signal, at least a first capacitor of the plurality of capacitors or at least a second capacitor of the plurality of capacitors is coupled to the non-rechargeable battery until a voltage level of the at least the first capacitor or of the at least the second capacitor reaches a power supply voltage level and is decoupled from the non-rechargeable battery after reaching the power supply voltage level.

18. The IMD of claim 15, further comprising:
 a counter coupled to the comparator, the counter configured to record a number of times the output signal is detected.

19. The IMD of claim 14, further comprising:
 a memory for storing data and executable instructions, wherein the executable instructions comprise code for causing the processor to:
  (a) conduct a communication session between the IMD and an external programming device, and
  (b) transmit count data from the IMD to the external programming device, wherein the external programming device is configured to determine a remaining lifetime of the non-rechargeable battery based on the count data.

20. The IMD of claim 19, wherein the count data comprises a count of a number of times of discharge of capacitors of the plurality of capacitors.

\* \* \* \* \*

UNITED STATES PATENT AND TRADEMARK OFFICE
CERTIFICATE OF CORRECTION

PATENT NO. : 11,493,556 B2
APPLICATION NO. : 16/364918
DATED : November 8, 2022
INVENTOR(S) : Daran DeShazo It is certified that error appears in the above-identified patent and that said Letters Patent is hereby corrected as shown below:

In the Specification

At Column 1, Line number 12, delete "rates, Implantable" and replace with --rates. Implantable--.
At Column 2, Line number 66, delete "patient: wireless" and replace with --patient; wireless--.
At Column 4, Line number 2, delete "interval: monitoring" and replace with --interval; monitoring--.
At Column 4, Line number 61, delete "neurormodulation" and replace with --neuromodulation--.
At Column 7, Line number 9, delete "after" and replace with --alter--.
At Column 7, Line number 19, delete "RE" and replace with --RF--.
At Column 7, Line number 30, delete "MULTIPROGRAMMABLE" and replace with --MULTI-PROGRAMMABLE--.
At Column 9, Line number 9, delete "IP G" and replace with --IPG--.
At Column 13, Line number 4, delete "drain in" and replace with --drain. In--.
At Column 13, Line number 47, delete "902, However" and replace with --902. However--.
At Column 13, Line number 65, delete "hi step" and replace with --in step--.
At Column 15, delete "35 § 112(f)" and replace with --35 U.S.C. § 112(f)--.

Signed and Sealed this
Tenth Day of January, 2023

Katherine Kelly Vidal
*Director of the United States Patent and Trademark Office*